US00PP35834P3

(12) United States Plant Patent
Arts

(10) Patent No.: US PP35,834 P3
(45) Date of Patent: May 28, 2024

(54) RASPBERRY PLANT NAMED 'ABB 132'

(50) Latin Name: ***Rubus. idaeus* L.**
Varietal Denomination: ABB 132

(71) Applicant: Allberry B.V., JJ Hedel (NL)

(72) Inventor: Niels Arts, De Kwakel (NL)

(73) Assignee: Allberry B.V., JJ Hedel (NL)

( * ) Notice: Subject to any disclaimer, the term of this patent is extended or adjusted under 35 U.S.C. 154(b) by 0 days.

(21) Appl. No.: 18/445,158

(22) Filed: May 2, 2023

(65) Prior Publication Data

US 2023/0371411 P1 Nov. 16, 2023

(30) Foreign Application Priority Data

May 4, 2022 (QZ) ..... PBR 20221155

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./203, 204
See application file for complete search history.

(56) References Cited

U.S. PATENT DOCUMENTS

PP23,914 P2 9/2013 Smaal et al.

*Primary Examiner* — Susan McCormick Ewoldt
(74) *Attorney, Agent, or Firm* — Plant & Planet Law Firm

(57) ABSTRACT

The new and distinct variety of raspberry plant variety 'ABB 132' is provided. The variety can be distinguished by its outstanding features of early autumn production, high productivity, and easily regrown after mow down.

3 Drawing Sheets

Latin name of the genus and species:
Botanical classification:
a. Genus—*Rubus.*
b. Species—*idaeus* L.
Variety denomination: The new raspberry plant claimed is of the variety denominated 'ABB 132'.

CROSS REFERENCE TO RELATED APPLICATIONS

This application claims the benefit of priority under 35 USC § 119 to Community Plant Variety Office (CPVO) Application No. 20221155 for Community Plant Variety Rights, filed on May 4, 2022, for a raspberry plant with a variety denomination of 'ABB 132', which is herein incorporated by reference in its entirety.

BACKGROUND OF THE INVENTION

Field of the Invention

The present invention relates to a new and distinct variety of raspberry plant, which has been given the variety denomination of 'ABB 132'.

Background of the Related Art

Raspberries are the edible fruit of a multitude of plant species in the genus *Rubus* of the rose family. Most raspberry species are in the subgenus *Idaeobatus*. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries in a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warmer climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purees, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

The present invention relates to a new and distinct variety of raspberry, which has been given the variety denomination of 'ABB 132' and is intended for use as fresh fruit.

The new raspberry variety is a selection resulting from a sexual cross of raspberry plants at De Kwakel, Netherlands in 2014, involving a seed parent known as '22' (unpatented) and a pollen parent known as '211157-009' (unpatented).

The selection was subsequently evaluated for a number of years at Rossum, Netherlands.

Asexual reproduction of the new variety by cutting propagation since 2016 at Rossum, Netherlands has demonstrated that the new variety reproduces true to type with all of the morphological characteristics, as herein described, firmly fixed and retained through successive generations of such asexual propagation.

Selection criteria included earliness, productivity, fruit color.

The following characteristics of the new variety have been repeatedly observed and can be used to distinguish 'ABB 132' as a new and distinct variety of raspberry plant: early autumn production, high productivity, easily regrown after mow down.

Plants of the new variety differ from plants of the seed parent '22' as set forth in Table 1. Pollen parent '211157-009' (unpatented) no longer exists so plants of the new variety were compared to plants of similar selection 'Advabertwee.' (U.S. Plant Pat. No. 23,914). Plants of the new variety differ from plants of 'Advabertwee' as set forth in Table 2.

TABLE 1

| Seed parent | Characteristics | Similar variety level of expression | Candidate variety level of expression |
|---|---|---|---|
| '22' | Spines | Medium | Same |
| '22' | Color fruit | Medium | Same |
| '22' | Earliness primocane | Early | Early |
| '22' | Fruit shape | Unregular shape | Nice shape |

TABLE 2

| Similar variety | Characteristics | Similar variety level of expression | Candidate variety level of expression |
|---|---|---|---|
| 'Advabertwee' | Spines | Medium | Same |
| 'Advabertwee' | Color fruit | Medium | Same |
| 'Advabertwee' | Earliness primocane | Mid-late | Early |
| 'Advabertwee' | Fruit firmness | Very firm | Firm |
| 'Advabertwee' | Primocane productivity | Medium-high | High |

BRIEF DESCRIPTION OF THE DRAWINGS

The accompanying photographic illustrations show the typical appearance of the new variety 'ABB 132'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
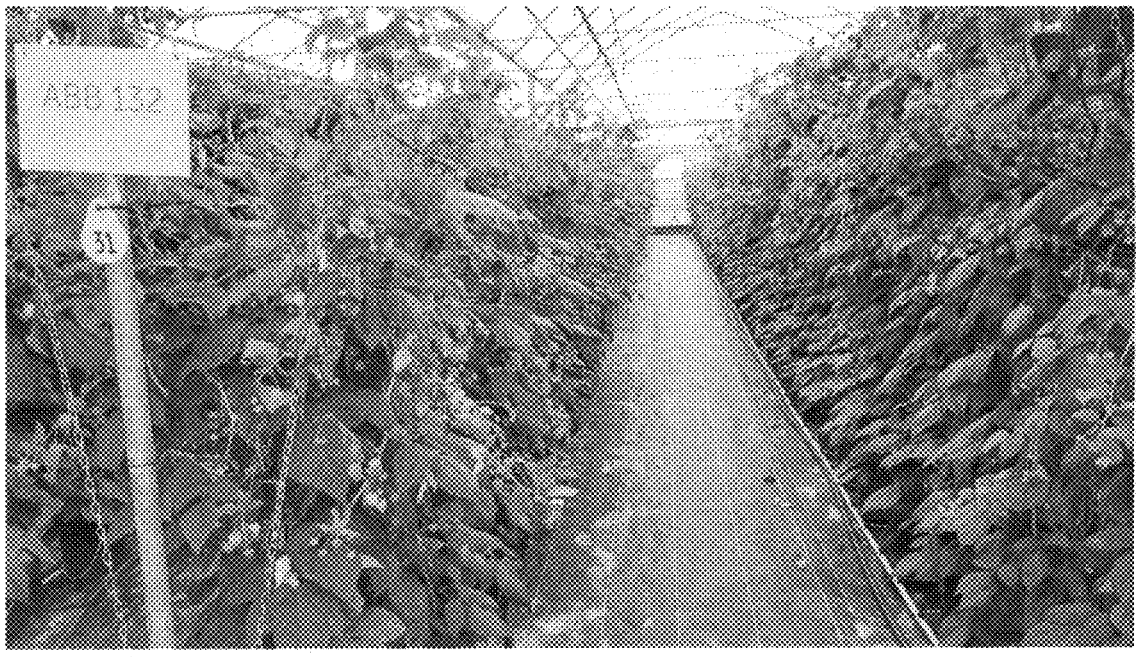
FIG. 1 is a photograph of the new variety 'ABB 132', demonstrating flowering from top to lowest bud (true primocane).
Figure 2:
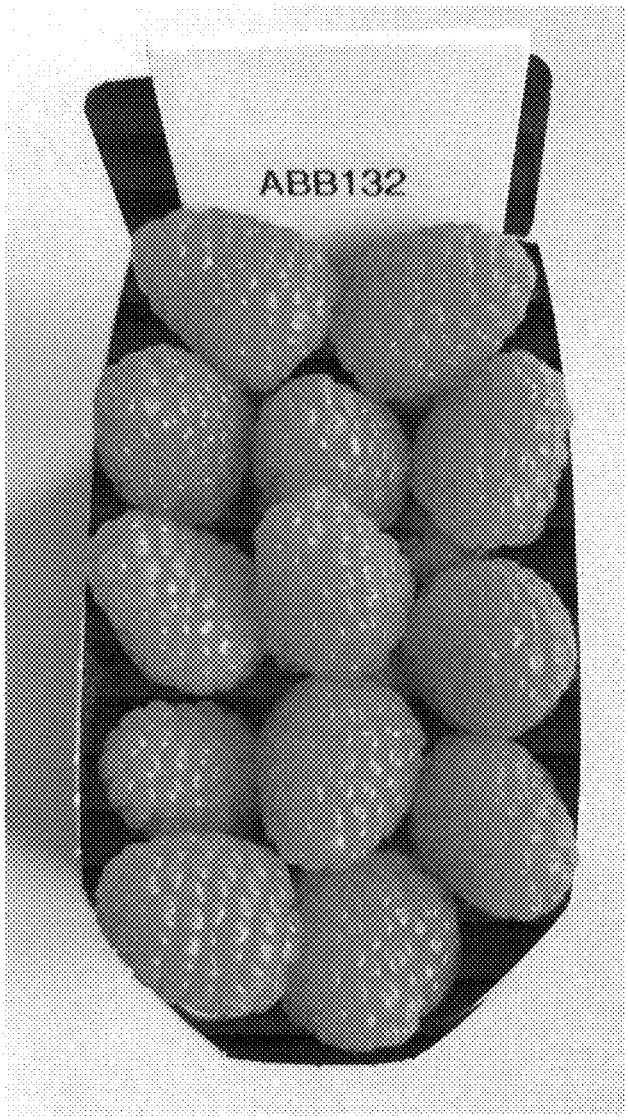
FIG. 2 is a photograph of the fruit new variety 'ABB 132'.
Figure 3:
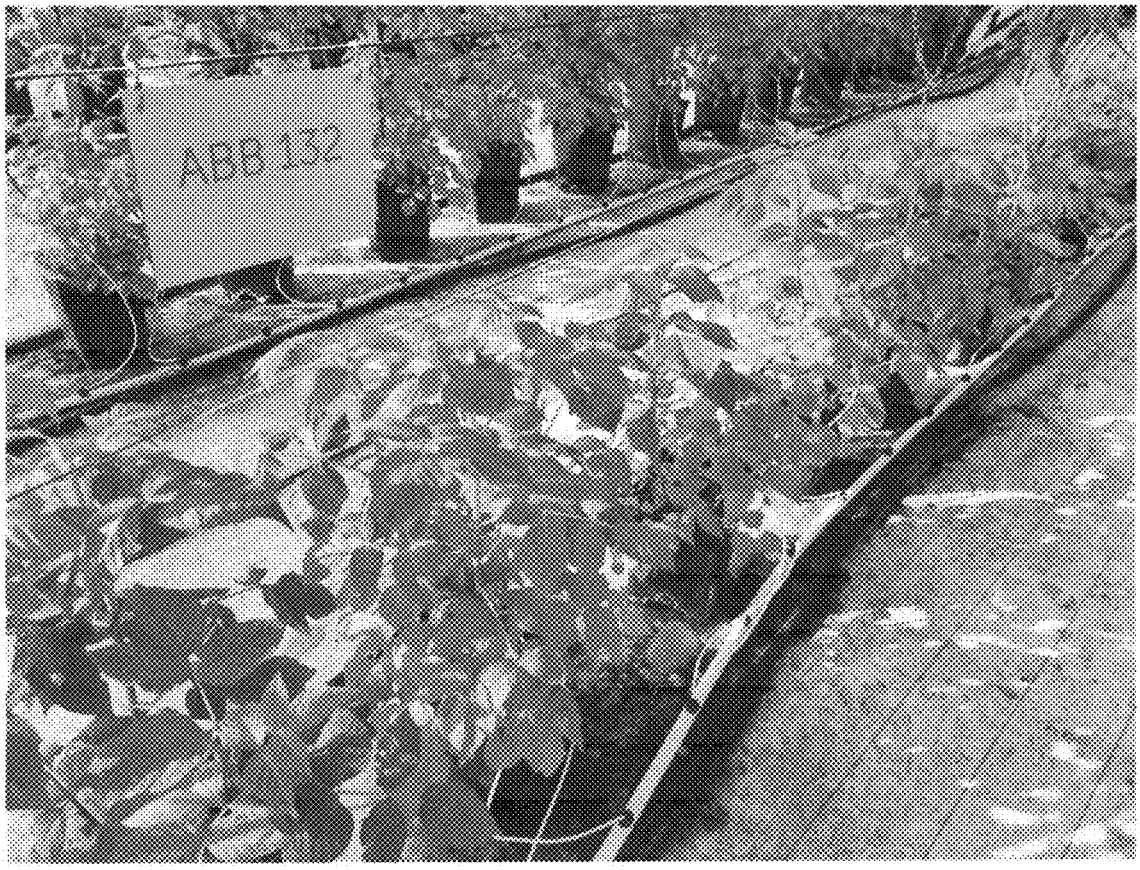
FIG. 3 is a photograph of new variety 'ABB 132', demonstrating rapid regrowth after mow down.

The following detailed description sets forth the distinctive characteristics of 'ABB 132'. The datum which defines these characteristics was collected from asexual reproductions of the original selection. Dimensions, sizes, colors, and other characteristics are approximations and averages set forth as accurately as possible. The plant history was taken on plants approximately 16 weeks, and the descriptions relate to plants grown in Rossum, Netherlands. Color notations are in reference to the standard R.H.S. Colour Chart 2015.

Classification:

a. *Family*.—Rosaceae.
b. *Botanical*.—*Rubus ideaus* L.
c. *Common name*.—Raspberry.
d. *Variety name*.—'ABB 132'.

Parentage:

a. *Female parent*.—'22'.
b. *Male parent*.—'211157-009'.

PLANT

General:

a. *Height*.—150-200 cm.
b. *Width*.—80-100 cm.
c. *Length/width ratio*.—Average.
d. *Growth habit*.—Upright.
e. *Primocane* (*current year's cane*).—i. Color — Green-135D. ii. Cane length in autumn —150-200 cm. iii. Internodal distance at central ⅓ of cane — 7 cm. iv. Anthocyanin coloration of cane — Absent. v. Cane bloom — Very strong. vi. Time of cane emergence — Early. 3-4 months. vii. Diameter — 10-20 mm.
f. *Very young shoot*.—i. Anthocyanin coloration of apex during rapid growth — Very weak.
g. *Floricane* (*previous year's cane*).—i. Dormant cane color — Greyish brown-brown-174B. ii. Fruiting lateral attitude — Semi-erect. iii. Fruiting lateral length — Medium. iv. Diameter — 10-20 mm.
h. *Prickles* (*spines*).—i. Presence — Present. ii. Density — Medium. 3-5 spines per linear cm of cane. iii. Length at 1 inch in height at end of harvest (from base to tip) — Short. iv. Color — Purplish-brown-59A.
i. *Fruit storage life and shipping quality*.—Good. i. Number of days of storage life at cold/or room temperature — 8-15. ii. Chilling requirement — Yes.
j. *Market use*.—Fresh.

k. *Hardiness zone* (*heat/cold tolerance*).—Extremely wide range. USDA zones 7-10.

l. *Plant/fruit disease and pest resistance/susceptibility*.—Low vulnerability for mildew and low vulnerability for spider mites.

LEAVES

General:

a. *Predominant number of leaflets*.—3.

b. *Profile of leaflets in cross section*.—Straight, somewhat concave.

c. *Leaf rugosity*.—Weak.

d. *Color of upper side*.—Dark-139A.

e. *Color of lower side*.—Light greyish green-191A.

f. *Surface texture of upper side*.—Weak rugosity.

g. *Surface texture of lower side*.—Weak.

h. *Terminal leaflet*.—i. Length — Long. 5-8 cm. ii. Width — Medium. 4-6 cm. iii. Length/width ratio — Medium. iv. Margin — serrate. v. Overall shape — Rounded oval. vi. Apex shape — Acuminate. vii. Base shape — Elliptical oval.

i. *Lateral leaflets*.—i. Length — Long. 5-8 cm. ii. Width — Medium. 4-6 cm. iii. Length/width ratio — Medium. iv. Relative position of lateral leaflets — Touching. v. Margin — Serrate. vi. Overall shape — Rounded oval. vii. Apex shape —Acuminate. viii. Base shape —Elliptical-oval.

FLOWERS

General:

a. *Diameter*.—Medium. 1-2 cm.

b. *Petal*.—i. Length — Medium. 6-10 mm. ii. Width — Medium. 2-3 mm. iii. Length/width — Medium. iv. Color of upper side — 155C. v. Color of lower side — 155C. vi. Number of petals — 5. vii. Margin — Standard. viii. Shape of base — Straight. ix. Shape of apex — Conical. x. Texture — Silky.

c. *Peduncle*.—i. Anthocyanin coloration — Absent. ii. Length — 2-5 cm. iii. Diameter —0.5-2 mm. iv. Color — Light greyish green-191A.

FRUIT

General:

a. *Length*.—Long. 25-35 mm.

b. *Diameter*.—Wide. 15-25 mm.

c. *Length/width ratio*.—Wide.

d. *General shape in lateral view*.—(Broad) conical.

e. *Color*.—Light red-34A.

f. *Glossiness*.—Strong.

g. *Firmness*.—Strong.

h. *Adherence to plug*.—Weak.

i. *Size of single drupe*.—Small.

j. *Number of drupelets per berry*.—High. 80-150.

k. *Average weight per berry*.—5-6 grams.

PRODUCTION

General:

a. *Main bearing type*.—True Primocane.

b. *Primocane* (*current year's cane*).—i. Time of beginning of flowering — Very early. 14-15 weeks after planting. ii. Time of beginning of fruit ripening — Early. 3-4 weeks after flowering. iii. Length of fruiting period — Medium-long. 8-10 weeks. iv. Yield — High. 20-25 T/Ha.

c. *Floricane* (*previous year's cane*).—i. Time of vegetative bud burst — Immediate — 1 week after cutback. ii. Time of beginning of flowering — Medium. 8-10 weeks after bud break. iii. Time of beginning of fruit ripening — Early-medium. 3-4 weeks. iv. Yield — Medium 5-10 T/Ha.

The invention claimed is:

1. A new and distinct variety of raspberry plant named 'ABB 132', as illustrated and described herein.

* * * * *